US011071743B1

(12) United States Patent
Fahy

(10) Patent No.: US 11,071,743 B1
(45) Date of Patent: Jul. 27, 2021

(54) EFFECTIVE, NON-TOXIC TREATMENTS FOR BRAIN CANCER

(71) Applicant: Gregory M. Fahy, Corona, CA (US)

(72) Inventor: Gregory M. Fahy, Corona, CA (US)

( * ) Notice: Subject to any disclaimer, the term of this patent is extended or adjusted under 35 U.S.C. 154(b) by 0 days.

(21) Appl. No.: 14/997,397

(22) Filed: Jan. 15, 2016

Related U.S. Application Data

(60) Provisional application No. 62/104,366, filed on Jan. 16, 2015.

(51) Int. Cl.
A61K 31/59 (2006.01)
A61K 31/522 (2006.01)
A61K 31/4045 (2006.01)
A61K 31/05 (2006.01)
A61K 31/01 (2006.01)
A61K 31/593 (2006.01)
A61K 31/155 (2006.01)
A61K 31/12 (2006.01)
A61K 31/19 (2006.01)
A61K 31/517 (2006.01)

(52) U.S. Cl.
CPC ............. A61K 31/59 (2013.01); A61K 31/01 (2013.01); A61K 31/05 (2013.01); A61K 31/12 (2013.01); A61K 31/155 (2013.01); A61K 31/19 (2013.01); A61K 31/4045 (2013.01); A61K 31/517 (2013.01); A61K 31/522 (2013.01); A61K 31/593 (2013.01)

(58) Field of Classification Search
None
See application file for complete search history.

(56) References Cited

U.S. PATENT DOCUMENTS 5,804,573 A * 9/1998 Silver .................. A61K 9/2013
514/167

OTHER PUBLICATIONS

Soderberg-Naucler et al. "Survival in Patients with Glioblastoma Receiving Valganciclovir". N Engl J Med. Sep. 2013;369:985-986.*
Trouillas et al. "Redifferentiation Therapy in Brain Tumours: Long-Lasting Complete Regression of Glioblastomas and an Anaplastic Astrocytoma under Long Term 1-Alpha-Hydroxycholecalciferol". Journal of Neuro-Oncology. 2001; 51:57-66.*
Martin et al. "Intracellular Signaling Pathways Involved in the Cell Growth Inhibition of Glioma Cells by Melatonin". Cancer Res. 2006; 66(2):1081-1088.*
Grobben et al. "Rat C6 Glioma as Experimental Model System for the Study of Glioblastoma Growth and Invasion". Cell Tissue Res. 2002;310:257-270.*
STN Registry No. 41294-56-8. "Alfacalcidol". STN Registry File. Retrieved Jan. 5, 2017. One Page.*
Tuzgen et al. "Relationship Between DNA Damage and Total Antioxidant Capacity in Patients with Glioblastoma Multiforme". Clinical Oncology. 2007; 19:177-181.*
Khan et al. "Cancer Chemoprevention Through Dietary Antioxidants: Progress and Promise". Antioxidants and Redox Signaling. 2008; 10(3):475-510.*
Dikalov et al. "Honokiol is a Potent Scavenger of Superoxide and Peroxyl Radicals". Biochemical Pharmacology. 2008; 76:589-596.*
Shoba et al. "Influence of Piperine on the Pharmacokinetics of Curcumin in Animals and Human Volunteers". Planta Medica. 1998;64:353-356.*
Wiltshire et al. "Pharmacokinetic Profile of Ganciclovir After its Oral Administration and From its Prodrug, Valganciclovir, in Solid Organ Transplant Recipients". Clin Pharmacokinet. 2005; 44(5):495-507.*
Magrassi et al. "Vitamin D Metabolites Activate the Sphingomyelin Pathway and Induce Death of Glioblastoma Cells". Acta Neurochir. 1998; 140:707-714.*
Joshi et al. "Vitamin D Deficiency in Adults". Aust Prescr. 2010; 33:103-106. (Year: 2010).*
Soderberg-Naucler et al. "Survival in Patients with Glioblastoma Receiving Valganciclovir". N Engl J Med. 2013; 369:985-986, Supplementary Appendix (p. 1-5). (Year: 2013).*
Draper et al. "Antioxidants and Cancer". Journal of Agricultural and Food Chemistry. 1984; 32(3):433-435. (Year: 1984).*
Random House Webster's College Dictionary. "Inoperable". 1991. p. 695. (Year: 1991).*
National Cancer Institute Dictionary of Cancer Terms [Online], "Inoperable". [Retrieved Dec. 18, 2019], Retrieved from the Internet: <URL: https://www.cancer.gov/publications/dictionaries/cancer-terms/def/inoperable>. One page. (Year: 2019).*
National Organization for Rare Disorders [Online], "Glioma". [Retrieved Dec. 18, 2019], Retrieved from the Internet: <URL: https://rarediseases.org/rare-diseases/glioma>. pp. 1-17. (Year: 2019).*
Harsh et al. "Thymidine Kinase Activation of Ganciclovir in Recurrent Malignant Gliomas: A Gene-Marking and Neuropathological Study". J Neurosurg. 2000; 92:804-811. (Year: 2000).*
Rainov et al. "Immune Response Induced by Retrovirus-Mediated HSV-tk/GCV Pharmacogene Therapy in Patients with Glioblastoma Multiforme". Gene Therapy. 2000; 7:1853-1858. (Year: 2000).*
Smitt et al. "Treatment of Relapsed Malignant Glioma with an Adenoviral Vector Containing the Herpes Simplex Thymidine Kinase Gene Followed by Ganciclovir". Molecular Therapy. 2003; 7(6):851-858. (Year: 2003).*
Westphal et al. "Adenovirus-Mediated Gene Therapy with Sitimagene Ceradenovec Followed by Intravenous Ganciclovir for Patients with Operable High-Grade Glioma (ASPECT): A Randomized, Open-Label, Phase 3 Trial". Lancet Oncol. 2013; 14:823-833. (Year: 2013).*
Stragliotto et al., "Effects of valganciclovir as an add-on therapy in patients with cytomegalovirus-positive glioblastoma: A randomized, double-blind, hyopthesis-generating study", International Journal of Cancer, 133, 1204-1214 (2013).

(Continued)

Primary Examiner — Leslie A. Royds Draper
(74) Attorney, Agent, or Firm — Donald E. Stout; Stout, Uxa & Buyan, LLP

(57) ABSTRACT

The current invention involves administration to a cancer patient of a combination of therapeutic agents that, as a combination, has more efficacy against brain cancer than any currently available chemotherapeutic agent or chemotherapeutic combination, and that has essentially no toxic effects.

5 Claims, 1 Drawing Sheet

(56) References Cited

OTHER PUBLICATIONS

Brewer et al., "Vitamin D Hormone confers Neuroprotection in Parallel with Downregulation of L-Type Calcium Channel Expression in Hippocampal Neurons", The Journal of Neuroscience, Jan. 1, 2001, 21 (1:98-108).
Zhang et al., "Overexpression of Copper Zinc Superoxide Dismutase Suppresses Human Glioma Cell Growth", Cancer Research 62, 1205-1212, Feb. 15, 2002.
Mulpur et al., "Complementary Therapy and Survival in Glioblastoma", Neuro-Oncology Practice, 2(3), 122-126 (May 6, 2015).
Heaney et al., "25-Hydroxylation of Vitamin D3: Relation to Circulating Vitamin D3 Under Various Input Conditions", American Journal of Clinical Nutrition, 2008, 1738-1742.
Product Monograph, "One Alpha—Alfacalcidol"—Leo Pharma Inc., Variation No. 34, Dec. 19, 2011.
"Vitamin D", Wikipedia, https://en.wikipedia.org/wiki/Vitamin_D, Apr. 12, 2018.
Sheam et al., "Protein Damage from Electrophiles and Oxidants in Lungs of Mice Chronically Exposed to the Tumor Promoter Butylated Hydroxytoluene", Chem Biol Interact, Jul. 15, 2011; 192(3)278-86.

\* cited by examiner

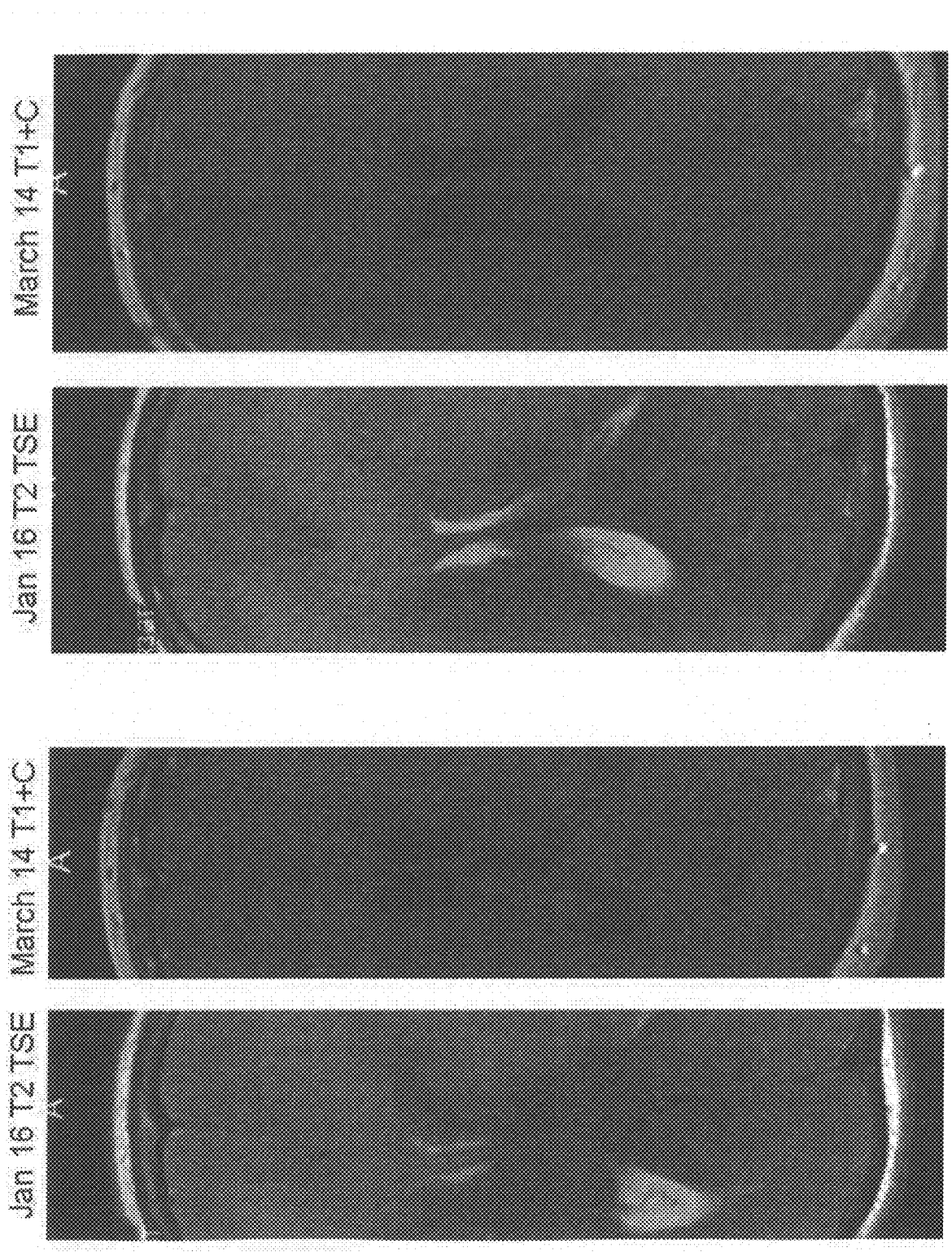

EFFECTIVE, NON-TOXIC TREATMENTS FOR BRAIN CANCER

CROSS-REFERENCE TO RELATED APPLICATIONS

This application claims from the benefit of U.S. Provisional Application No. 62/104,366, filed on Jan. 16, 2015 and entitled EFFECTIVE, NON-TOXIC TREATMENT FOR HUMAN BRAIN CANCER, the entire contents of which are herein expressly incorporated by reference.

BACKGROUND OF THE INVENTION

Brain cancer is one of the worst nightmares imaginable, both for the patient and for the family of the patient. This is a disease that targets the core of what it means to be a human being. Nevertheless, there is no adequately effective treatment for human brain cancer.

Human brain cancers include glioblastoma, glioblastoma multiforme, anaplastic astrocytoma, and related conditions. Radiation can extend median life expectancy to about one year, and the combination of temozolomide and radiation can extend median life expectancy to about 14 months, but temozolomide is only effective (and then only weakly) in a relatively small minority of patients, and radiation has severe side effects, is frequently ineffective, and is handicapped by the distributed nature of these cancers, which invade brain tissue finely, such that radiating the cancer requires radiation of the surviving normal brain tissue as well. Furthermore, almost all patients eventually die as a result of the disease and its treatment. Although there are differences between different kinds of primary brain cancer, their similarities are greater than their differences, and, for example, the treatment of anaplastic astrocytomas is the same as the treatment of glioblastomas. For purposes of the present application, the word "glioblastomas" will usually be used to refer both to glioblastomas per se and all other primary brain cancers having properties similar to those of glioblastomas per se.

Cancers are the result of genetic damage. There is an impetus to better characterize all forms of cancer with respect to their genetic causes so as to be able to select drugs for therapy that are better tailored to the causes of the problems than the current "blunderbuss" approach of using, for example, colon cancer drugs to treat colon cancer even if a particular colon cancer might actually have mutations that would be better treated with a drug for breast cancer or the like. However, cancer is a "moving target" in that therapies directed against a particular mutation may be nullified or circumvented by additional mutations. Further, many chemotherapeutic agents have bad side effects, and many are mutagenic, which is not ideal for the treatment of a disease that is caused by mutations and whose ability to evade death from treatment depends in significant part on additional mutations. Further, many kinds of cancer, most prominently brain cancer, have no effective drugs to select from at this time.

Biotechnological approaches to treating cancer have great promise as potentially specific, side-effect free "magic bullets" tailored specifically to the cancer and not to normal tissue, but these future breakthroughs are years away and will be costly. Immunological approaches are highly promising, but are currently unavailable for widespread use, and will likely remain so for years. Furthermore, in the specific case of brain cancer, inflammation resulting from immune attacks on the cancer may cause brain swelling, which could be fatal in and of itself due to the inability of the brain to swell significantly without having its blood flow curtailed. Furthermore, the blood-brain barrier may inhibit some immunotherapies, although it is possible for immune cells to cross that barrier.

There are many treatments that have been found to have weak and frequently unconfirmed effectiveness against glioblastomas, usually in studies involving relatively new patients. Virtually all of these were summarized in 2002 in the book, "Surviving 'Terminal' Cancer: Clinical Trials, Drug Cocktails, and Other Treatments Your Doctor Won't Tell You About" [1] and then again in 2013 in an excellent update on the subject, "Treatment Options for Glioblastoma and Other Gliomas," by Ben A. Williams [2]. Unfortunately, none of these treatments is even remotely adequate, and there remains no established treatment for human brain cancer that is better than the dismal combination of surgery, radiation, and temozolomide chemotherapy. Folklore about treatments such as cannabinoid therapy does not seem to be borne out by any available objective evidence.

The incentive to develop an effective treatment has been immense for very many years. The fact that no such therapy has been previously developed is therefore excellent evidence of the novelty and lack of obviousness of the present invention.

The present invention overcomes past failures and provides a very surprisingly effective and novel treatment even for advanced, inoperable brain cancer, without significant side effects or risks. The present invention was driven by the inventor's personal experience with a particularly desperate case of anaplastic astrocytoma that required an intense and creative attempt to create a medically acceptable solution that could be put into use immediately. The effectiveness of the present invention is completely unpredictable, and was in fact considered highly implausible by all doctors associated with its successful demonstration until its efficacy became obvious due to the results achieved.

SUMMARY OF THE INVENTION

The current invention is a novel combination of therapeutic agents that, as a combination, has more efficacy against brain cancer than any currently available chemotherapeutic agent or chemotherapeutic combination, and that has essentially no toxic effects. The best progression-free survival obtained with the state of the art "Stupp protocol" (radiation, surgery, and temozolomide chemotherapy) is about 7 months, and the mean survival time is about 14 months from time of diagnosis when diagnosis is not delayed until close to the time of death. The present invention has halted progression in one glioblastoma multiforme patient after about 9 months of prior progression, and permitted progression-free survival thereafter for an additional 15 months, yielding a total survival time of 24 months as of the date of this application, with the patient in apparently good health other than some dizziness caused by partial resection of his cerebellum immediately after initial diagnosis. In another case, a patient with enormous brain distortion caused by a highly advanced anaplastic astrocytoma and suspected brain herniation event caused by the tumor experienced near-complete reversal of the brain distortion, was successfully removed from her respirator, and regained the ability to speak, walk, and use the formerly paralyzed right side of her body within 2 months of the onset of treatment. Eventual death 14 months after the onset of treatment was associated with events stemming from a prior interruption of the treatment, leading to progression followed by radiation that precluded continued adequate oral intake of treatment medications.

The new treatments are based on three previously unproven hypotheses. The results validate these hypotheses far beyond the expectations of even the inventor.

Hypothesis 1: it might be possible to defeat brain cancer by combining multiple individually inadequate yet partially effective therapies. The ineffectiveness of mono-therapies may be due to a) the genetic instability of cancer, which generally allows it to "adapt" to mono-therapies by mutating so as to escape the effects of treatment, and b) the fact that each individual mono-therapy only addresses part of the problem, whereas perhaps the combination of many mono-therapies applied simultaneously could target enough vulnerabilities to destroy the cancer. If the probability of evading therapy a is p1, then the probability of simultaneously evading therapies a-d might be p1 times p2 times p3 times p4, or dramatically lower than the likelihood of escaping from any one mono-therapy alone. Similarly, if the likelihood of inadequacy of targeted mechanism a is p5, and the likelihood of inadequacy of targeted mechanism b is p6, and so on, the likelihood of the inadequacy of therapies a-d in combination may be p5 times p6 times p7 times p8, and, overall, the probability of cancer survival of the combination of a-d may be the product of p1, p2, p3, . . . , p9, or, again, far better than can be achieved by any one therapy alone. Furthermore, this may be an underestimate because the time available for evasion of any one treatment is also reduced by the fact that all other treatments are simultaneously reducing tumor viability or proliferative ability.

Still, choosing which therapies to combine is not straightforward. The number of possible combinations is astronomical, and there is little to no guidance as to which combinations will be most advantageous. The present invention was derived using Hypothesis 2.

Hypothesis 2A: the best candidate therapies are those that have allowed prolonged survival of at least a subset of treated subjects, even if that surviving population is a small fraction of the total. If treatment A allows 20% of patients to survive, treatment B allows 30% of patients to survive, and treatment C allows 50% of patients to survive, and if treatments A, B, and C work by means of completely independent mechanisms of action but are not incompatible with one another, then there is a reasonable chance that combining A with B and C will result in the survival of most patients. Patients are genetically diverse, and a given treatment may work well with some genotypes but not with others, but if mechanistically different treatments work on different population subsets, then a combination of those treatments may work on most patients.

Hypothesis 2B: Even if treatments D, E, and F have not been shown to extend survival of brain cancer patients, but are likely to damage glioblastomas by independent mechanisms, and are likely not to be incompatible with A, B, and C, then adding them, individually or collectively, to A and B and C should be more effective still.

Regardless of the validity of Hypotheses 1 and 2, however, putative interventions will be of no benefit if doctors are not willing to act on them. The present inventor faced this reality when selecting treatments to propose to the medical staff at the Stanford University Medical Center in a last-ditch effort to save the life of his sister-in-law. Given the general reluctance of medical practitioners to expose themselves to legal liability and to expose their patients to treatments that have not been established by large pre-existing clinical trials, the only possible way to gain acceptance of a proposal to intervene in a novel way is to propose only agents that are already known to be safe and of no serious concern. The consequence of this highly practical fact is Hypothesis 3.

Hypothesis 3: there exist candidate therapies consistent with Hypothesis 1 and Hypothesis 2 that are acceptably non-toxic to the patient, such that doctors can prescribe them or at least permit them without serious concerns. These are the correct candidate therapies to select to compose an overall combination therapy that can achieve immediate practical success.

Another reason to select therapeutic modalities that are clearly benign is that they may have the potential to be purchased and used outside of conventional medical practice and FDA scrutiny. In other words, a therapy can only be attempted if access to that candidate therapy is available. In the United States, there is a large health food/dietary supplement industry that enables an inventive person to purchase many substances that might be interesting to test in a therapeutic mode, without the need for FDA approval and, if necessary, although undesirably, even without the permission of an attending physician. As long as the treatments are benign, even in the context of the disease state and the other independent treatments thereof, there is no harm to be done, and no ethical barrier to using such treatments. This perspective has, as described below, contributed to the inventive process of the present invention, even if FDA approval will ultimately be necessary for the broad deployment of the current invention.

The present invention involves, as alluded to above, several components. The invention may be practiced at different levels of intensity depending on the particular circumstances of individual patients, involving the inclusion of fewer or more numerous interventions, as follows.

The most basic treatment involves administration of a combination of valganciclovir (or its equivalent), alfacalcidol, and melatonin, with or without the inclusion of butylated hydroxytoluene (or BHT). This combination may be referred to as the "core treatment."

The second level of treatment involves adding any or all of lycopene, curcumin, honokiol, or resveratrol to the core treatment, and preferably involves the addition of all four of these extra agents. The curcumin is preferably a version of curcumin modified to enable enhanced absorption (bioavailability).

The third level of treatment involves adding any of metformin plus a statin, dichloroacetate (DCA), or a combination of these two interventions to either the core treatment or to the second treatment level regimen, preferably the latter.

A fourth level of treatment involves adding an epidermal growth factor inhibitor such as Erlotinib to the third level of treatment when the third level of treatment includes metformin plus a statin.

At any level of treatment, if alfacalcidol is temporarily or permanently not available, it can less preferably be replaced with high-dose vitamin D3 (2000-30000 IU), especially at the second and third levels of treatment, as validated in Example 2 below.

It is believed that the treatments of the present invention can be carried out more conveniently using special formulations of the treatment medications of the invention. Such special formulations will be described in a continuation-in-part of the present application.

BRIEF DESCRIPTION OF THE DRAWINGS

The drawing FIGURE shows magnetic resonance images (MRI) of a human brain before and after administration of the core treatment which is the subject of this patent application, including delayed inclusion of BHT and then of resveratrol, wherein the MRI's are taken approximately two months apart.

DETAILED DESCRIPTION OF THE INVENTION

The invention consists of a combination of therapeutic agents that kills and arrests brain cancer more effectively than any one agent can on its own, and more effectively than any currently available chemotherapeutic regimen, and with virtually no side effects. The invention can be practiced at multiple levels, with increasing effectiveness as the intensity, or level, of treatment is increased.

The "core treatment" (lowest level of highly effective treatment) involves the following therapeutic agent combination, and the following nominal doses for each member of the core treatment group:

Valganciclovir: 450 mg twice a day (or another anti-CMV agent in CMV-inhibitory equivalent doses);
Melatonin: 10 mg twice a day or 20 mg once a day;
Alfacalcidol: 3 micrograms/day; and preferably, but optionally,
BHT: 350-700 mg twice a day, or 700 mg once a day plus 350 once a day;

with the following useful dosage ranges:

Valganciclovir: 200-800 mg twice a day (or the equivalent thereof)
Melatonin: 5-20 mg twice a day;
Alfacalcidol: 0.5-10 micrograms per day, in single or divided doses; and
BHT: 100-2000 mg/day.

The second level of treatment adds any or all, but preferably all, of the following agents to the core treatment in the following nominal doses and dose ranges:

Lycopene: 8 or 15 mg once a day (4-30 mg/day in single or divided doses)
Curcumin: super bio-absorbable curcumin (such as Super Bio-Curcumin, as sold by the Life Extension Foundation in Florida), 400 mg twice a day (200-1000 mg twice a day)
Honokiol: 250-1000 mg, 1-4 times per day (100-4000 mg/day, preferably with food) and
Resveratrol: 250 mg twice a day nominal, or 100-1000 mg per day in total as a useful range.

The third level of treatment adds:

DCA: 5-15 mg/kg (ideally, 12.5 mg/kg) once or preferably twice per day until peripheral numbness (nephropathy) develops, after which the dose is to be reduced to, nominally, 6.25 mg/kg (4-8 mg/kg) twice a day;
and/or
A statin, preferably lovastatin (ideally, 850 mg once a day, or a range of 20-1000 mg a day, which greatly exceeds the typical 20-40 mg dose used for prevention of heart and vascular disease), but any statin that inhibits the MAP kinase pathway and penetrates the brain at rates comparable to or superior to the brain uptake rates of lovastain [3], in doses equivalent to the above lovastatin doses in their effect on MAP kinase pathway inhibition, will be effective in the invention, plus
metformin (500 or 850 mg twice a day; useful range, 250-1000 mg twice a day), or its equivalent in terms of mTOR inhibition.

The fourth level of treatment adds, specifically to the statin plus metformin combination of the third level of treatment, Erlotinib, in a dose sufficient to inhibit the epidermal growth factor pathway clinically and in a clinically acceptable dosage range per day.

The adjunct agent, vitamin D3, is to be given at 2,000-30,000 IU/day. If alfacalcidol is also given, then vitamin D3 should be given in the evening if alfacalcidol is given in the morning, and vice versa. If alfacalcidol is not available, vitamin D3 should be given instead.

The Theory Behind the Invention

Valganciclovir [4], alfacalcidol [5], and melatonin [6] are included because they have individually been reported as being effective for a minority of glioblastoma victims in their own right, as per Hypothesis 2A. None of these agents has been adopted for routine use to the knowledge of the inventor due to skepticism over their effectiveness and their use only on small numbers of patients. They have never before been considered as a combination treatment, nor could the spectacular effectiveness of this particular combination, as indicated by FIG. 1 and Example 2, have been predicted from any previously known information. This combination is the core of the invention and is believed to account for many, but not for all, of its benefits.

BHT is added as an adjunct on the theory that it may either facilitate the action of valganciclovir or its equivalent or, if valganciclovir or its equivalent is not available, substitute for it.

Valganciclovir is an antiviral agent, being particularly known for its action against cytomegalovirus, which is a lipid-encapsulated virus. BHT has been reported to kill lipid-encapsulated viruses in vitro [7]. It was theorized for the present invention that it may have anti-viral activities that are complementary to those of valganciclovir, thus making valganciclovir a more effective anti-glioblastoma agent when used in combination with BHT, and offering an alternative to valganciclovir when necessary. Valganciclovir is also an extremely expensive drug, whereas BHT is extremely inexpensive and is regarded in the present invention as a "poor man's valganciclovir," but valganciclovir is still the agent of choice, with BHT providing additional possible help to the valganciclovir. In the prior art, there is no demonstration of the effectiveness of BHT against CMV in humans, so its use in the present invention was speculative and controversial.

Lycopene [8], curcumin (and especially "bio-absorbable" curcumin), and Honokiol are all valuable agents for the treatment of glioblastomas and all are non-toxic, so their combination with the core group, with or without BHT, is included to add effectiveness to the core treatment. The effectiveness of lycopene is distinct but slight in its own right, but is believed to be magnified when combined with the core group. Resveratrol, while having powerful anti-glioblastoma effects in lab dishes [9], penetrates the blood-brain barrier poorly if at all in normal brains [10]. It is included because glioblastomas tend to make the blood-brain barrier more permeable in the vicinity of the cancer, possibly allowing resveratrol to leak into the brain and help to kill the cancer. Resveratrol is very non-toxic and therefore is not harmful to include in the treatment mix.

DCA has given good results in one human trial [11], and therefore is favored in combination with the core group. DCA's mechanism of action does not overlap with that of any other agent in the core group, which is a significant advantage. DCA has not been used in the prior art in combination with any of the agents in the core group, let alone in combination with BHT.

Inclusion of the combination of metformin and a statin is based on the fundamental biology of glioblastomas. Glioblastomas are driven by signaling through the mTOR pathway, which is blocked by rapamycin or metformin, but rapamycin is self-limiting because it leads to activation of mTORC2 (and no mTORC2 inhibitors are yet approved by the FDA for clinical use), and metformin alone is without effectiveness because signaling through the MAP kinase pathway activates the final steps of the mTOR pathway, thus bypassing the effect of metformin [12]. The use of lovastatin can prevent this bypass of the mTOR pathway blockade, but use of lovastatin alone, while showing hints of efficacy [13], will be without major utility unless the mTOR pathway is independently blocked. The MAP kinase pathway can also be activated by signaling through the epidermal growth factor receptor (EGFR), but blocking this receptor by itself is ineffective. It is therefore provided by the present invention that the best result will be obtained when an EGFR inhibitor (fourth level of treatment) is combined with a statin and with metformin. But this approach, by itself, will still be severely limited, because a) it will take metformin a long time to accumulate to a sufficient level in the brain to be effective [14], and b) it will take a statin such as lovastatin a very long time to accumulate in the brain sufficiently to have an appreciable effect [15], even when used at ~20 times the normal human clinical dose, which is required (and can be managed clinically [13], particularly in combination with coenzyme Q10 administration to block side effects) while c) an EGFR inhibitor's effectiveness will depend highly on the effectiveness of the statin and the mTOR path inhibitor. What is needed is to combine the agents of the third level treatment with the core group, so that the glioblastoma can be largely destroyed by the core group while both metformin and lovastatin (or their equivalents) are slowly accumulating in the brain to levels sufficient to destroy the cancer by completely unrelated mechanisms. With this plan, the combination of the core group and the third treatment level group will be effective with or without the other agents named in this invention, and has the advantage of being deployable today. In some cases, Honokiol may replace metformin in this treatment modality.

Vitamin D3 is considered optional due to the lack of direct evidence for its effectiveness against glioblastomas, but due to its physiological relationship to alfacalcicol, it is considered valuable particularly when alfacalcidol is not available, as a possible substitute. Example 2 below suggests that there is no antagonism between vitamin D3 and alfacalcidol, so simultaneous use is possible.

It is emphasized that the methods and treatments of the present invention need not be applied in isolation. The present invention appears to be entirely consistent with and compatible with other treatment modalities, including conventional therapies and newer immunotherapies. It is postulated that the methods of the present invention will make other treatments more effective. Nevertheless, the current invention provides a valuable alternative when other therapies are either unavailable or, in the case of conventional treatments, ineffective.

The use and effectiveness of the treatments of the present invention are further explained in the context of the following Examples.

Example One: Treatment of a 57-Year-Old Female

Initial application of the core treatment, with rapid addition of BHT, and later the addition of the $2^{nd}$ and $3^{rd}$ levels of treatment, extended the life of a female patient, who had a projected life expectancy of approximately two days, to 14 months. This result was obtained under extreme conditions and resulted in the reversal of brain cancer growth and cancer effects such as aphasia and paralysis. The details follow.

A 57 year-old female patient was diagnosed with grade III anaplastic astrocytoma with suspicion of glioblastoma based on biopsy examination on Nov. 21, 2013, approximately one year and one month after initial symptoms were experienced but inappropriately attributed to other causes or to no cause. At the time of diagnosis by biopsy, the patient's three tumor foci were all inoperable due to their location and extent. Treatment was delayed for another two months by a change of treatment venue, the need to prepare for radiotherapy, and by the Thanksgiving, Christmas, and New Year's holidays.

The patient received two doses of radiation and one dose of chemotherapy with temozolomide on Jan. 13-14, 2014, before experiencing a seizure on January $14^{th}$ requiring immediate hospitalization. The following morning, she was believed to have experienced brain herniation, a common cause of death from brain tumors, since it prevents spontaneous breathing, and was treated with dexamethasone and hypertonic salt to reverse brain swelling. The family was informed that they would have to make a decision about whether to permanently withdraw artificial breathing support and let the patient die. A magnetic resonance image (MR image) showed massive intrusion of the cancer throughout the patient's brain, with massive left-right brain asymmetry caused by more tumor growth in the left side of the brain than in the right (FIG. 1, left images). The family was urged in very strong terms to withdraw life support and allow the patient to die peacefully at home.

Instead, in a group meeting involving the doctors, visiting intern, nurses, hospital pharmacy staff, and key family members, the present inventor was able to persuade the participants that the proposed treatment should be carefully considered. After private discussions between the present inventor and a particularly open-minded and objective visiting intern, in which the evidence for and against the core group of medications (valganciclovir plus alfacalcidol plus melatonin) was carefully examined, it was decided that the proposed treatment would be permitted. That evening, on January $16^{th}$, the core treatment was begun at the nominal doses described above.

The following day (Saturday), the new attending physician, who was not involved in the previous discussions and was completely unsympathetic to the notion that anything could be done for this patient, insisted vociferously that the treatment should be ended and the breathing tube should be removed, but finally conceded that if there was no strong objection by the other staff on Monday, the treatment would not be stopped. As it happened, the treatment was continued and, after additional meetings on Monday, the breathing tube was left in.

On the fourth day of treatment, the breathing tube was removed and was never again required. After a week of treatment, salt therapy was discontinued, the dexamethasone dose was reduced, and the patient was taken out of intensive care and transferred to the neurology ward.

In the neurology ward, BHT was added to the treatment regimen (completing the core treatment medication group) in clandestine fashion at a dose of 350 mg once or twice a day. She began talking again and regained the ability to walk and use the previously paralyzed right side of her body. Her nurses openly stated that this was a miracle and that she was never expected to be able to speak or walk again.

After a week in the neurology ward, she was discharged to a skilled nursing facility (SNF), and her dexamethasone dose was further reduced. At the time, the hospital physicians maintained that the only reason the patient was still alive was their use of dexamethasone to reverse tumor-induced brain swelling, so the predicted course could only have been a resumption of brain swelling due to ongoing tumor growth followed by re-herniation and death if the treatment of the present invention had been ineffective. Instead, the patient continued to regain more and more neural and physical function, and pentoxyffylin was added to the regimen at the suggestion of a consulting friend of the family and geriatrician to help make up for the tapering of the dexamethasone. The full dose of BHT, 350 mg twice a day, was instituted and made part of her official medical regimen, as was resveratrol.

The rule for remaining in the SNF was that steady progress must be made, indicating effectiveness of SNF rehabilitation with the medications of the invention. On the basis of this rule, the patient remained in the SNF for three weeks, and then was transferred to home care successfully.

The patient was given another MRI examination two months after her initial seizure and ostensible herniation event, in March of 2014. FIG. 1 shows a comparison between her MR images on the day the treatment of the current invention began (core treatment not including BHT) and her images two months later (core treatment including BHT, and also resveratrol and pentoxyffylin). The massive left-right brain asymmetry, indicated by displacement of the brain midline perhaps as much as an inch to the right side of her brain, as well as the virtual collapse and disappearance of her cerebral ventricles (shown as white areas in the pre-treatment images) caused by the expansion of brain tumor tissue at the expense of the ventricles, were completely reversed after two months of treatment. (In the post-treatment images, the ventricles appear black rather than white because a different MR imaging method was used, making it possible to compare only physical landmarks such as the brain midline and the size and shape of the ventricles between the two sets of images.) At this point, the neurooncologist in charge of this patient described the MRI results as "miraculous."

Five months after being given hours to days to live, and being given no chance to be able to walk and talk again, the patient was able to walk through a University of California campus on her own and watch and applaud and experience joy as her son graduated from college. She was also able to walk along the beach and a scenic pier, feed ducks at a local pond, and indicate to a waitress what she wanted for dinner at a local restaurant.

Tumor progression began after a period during which alfacalcidol became unavailable for a period of weeks. DCA was added to her regimen, and vitamin D3 as a substitute for alfacalcidol, but slow tumor progression continued. She became refractory to taking medications, including her anti-seizure medications, and was hospitalized with a seizure secondary to failure to take her full anti-seizure medication doses. She made a full recovery in the hospital, despite continued low dosing with anti-seizure agents for a few days, and was eating and talking and smiling again, but her doctors, mistaking the seizure as being an effect of tumor progression rather than failure to take her medications, ordered whole brain radiation, which resulted in even greater difficulty with swallowing and almost complete refusal to accept anti-seizure medications. The agents of the second treatment level were added about 7-8 months after her herniation diagnosis, and seemed to help considerably, but were hard to administer, and by the time the third treatment level agents were added, in fragmentary form (metformin plus low-dose (40 mg/day) lovastatin, no EGFR inhibitor), after about 10-11 months, medication administration had become essentially impossible.

She lived for 14 months after her diagnosis of imminent death, 16 months from the time of initial diagnosis, and 28 months from the time she SHOULD have been and normally would have been diagnosed, despite lack of any surgery or early radiation. Compared to an expected survival time of 14 months for conventional therapy, including early surgery and early radiation, from the time of an early diagnosis, her survival time was doubled, and presumably would have been much longer, and even indefinite, had her supply of alfacalcidol not been interrupted. Compared to her estimated survival time of circa 2 days just before the onset of the treatment of the current invention, her actual survival time was improved astronomically. Death was almost certainly significantly hastened as well by the aftereffects of possibly unnecessary and inappropriate total brain radiation at 7 months after herniation, which was followed by inability to eat, which prevented her from being able to take most of her medications.

Example Two: Treatment of a 40-Year-Old Male

The second case was treated with the benefit of the experience gained from Example One and provided evidence that lapses in alfacalcidol can be survived provided treatment levels 2 or 3, with simultaneous addition of vitamin D3, are in use at the time.

A 40 year old man living in Argentina was diagnosed with glioblastoma multiforme in January of 2014 and was immediately treated with surgery, chemotherapy, and radiation. Despite conventional therapy, MRI monitoring showed an increase in tumor size between February and June, and the patient's dose of dexamethasone was increased in July to prevent brain swelling. Continuation of conventional treatment resulted in additional progression of tumor growth as documented in September. Therefore, despite surgery, radiation, and temozolomide chemotherapy, there was no or essentially no period of non-progression within the first 8 months after early diagnosis.

Shortly thereafter, near the middle of October, the patient began receiving the following regimen, alfacalcidol not being available:
valganciclovir, 450 mg twice a day
melatonin, 12 mg twice a day
BHT, 700 mg in the morning plus 350 mg at night
resveratrol, 175 mg twice a day
lycopene, 15 mg once a day
Honokiol, 250 mg twice a day
metformin, 500 mg once a day, and
vitamin D3, 2800 IU at night.

At this time, the dose of dexamethasone was 4 mg in the morning and 2 mg in the evening.

About two weeks later, bio-absorbable curcumin (from the Life Extension Foundation, described above), 400 mg twice a day, was added to the regimen, and circa November $4^{th}$, alfacalcidol was added to the regimen (3 micrograms in the morning).

At that time, an MRI scan showed no tumor progression since the last scan in September, and temozolomide was discontinued. Two months later, in January 2015, about 3 months into the treatment of the present invention, the tumor mass appeared smaller or unchanged, and the dexamethasone dose was reduced to two mg twice a day. The supply of alfacalcidol ran out at about that time. At the same time, sugar and other carbohydrate intake was restricted. In February, the dexamethasone dose was cut to 1 and 2 mg in the morning and evening, respectively. In March, 5 months into the treatment, no tumor progression was seen, and the patient was continuing to do well. Alfacalcidol was resumed in April, at a double dose (3 micrograms twice a day) to compensate in part for the previous lapse, at which time the dexamethasone dose was cut to 1 mg twice a day. The tumor continued to show no progression in May, and the alfacalcidol dose was reduced to 2 micrograms twice a day in June, when the metformin dose was raised to 450 mg in the morning. In July, the tumor continued to show no progression. The evening dose of melatonin was increased to 15 mg as a possible sleep aid, the alfacalcidol was set back to 3 micrograms twice a day, and 350 mg of resveratrol was given in the morning. No other changes in the regimen were made.

DCA was added in mid-October at a dose of 12.5-15 mg/kg for about 3 weeks, paused for about 3 weeks, and then escalated to 22 mg/kg until numbness was experienced, after which the dose was dropped to 5 mg/kg and then discontinued temporarily circa mid to late December, 2015.

By January of 2016, or 15 months into the treatment of the present invention, tumor progression was still absent, and the patient continued to be doing well. The dexamethasone dose was slightly increased in October, but by January had been set back to 1 mg twice a day. Resveratrol was increased to 250 mg twice a day, curcumin to 630 mg twice a day, metformin to 800 mg once a day, and the evening melatonin dose was set to 20 mg. At that time, the BHT dose was 350 mg twice a day. Rosuvastatin was started at 10 mg/day.

In summary, fifteen months after the onset of the treatments of the invention (at the date of writing of this patent application), there was no tumor progression, and the patient appeared to be doing well clinically.

It should be noted that 15 months of no tumor progression is not expected for this aggressively growing cancer without special interventions, and progression-free survival had not been seen for several months prior to the onset of the treatment of the present invention, strongly indicating the effectiveness of the methods of the current invention, not only in an aging woman but also in a pre-middle-aged man.

In summary, what has been described in this application is as follows.

A safe and effective core treatment for human brain cancer, comprising administering a combination of valganciclovir, alfacalcidol, and melatonin to a human brain cancer patient.

An enhancement of this treatment wherein administration of butylated hydroxytoluene to a human brain cancer patient is added to the core treatment.

A further enhancement of the core treatment, comprising adding treatment with any or all of lycopene, curcumin, honokiol, and resveratrol, with or without the inclusion of BHT, and wherein the curcumin is preferably provided in a preparation designed to increase its absorption when ingested.

A further enhancement of the above treatments, comprising addition of treatment with dichloroacetate and/or the combination of metformin and a statin.

A further enhancement of the described treatments that include the use of a combination of metformin and a statin, comprising the addition of treatment with an epidermal growth factor inhibitor such as erlotinib.

The treatments described will also be effective if valganciclovir is replaced by another effective cytomegalovirus inhibitor, and/or if metformin is replaced by another effective mTOR inhibitor, and/or if alfacalcidol is temporarily discontinued and vitamin D3 is used to substitute for it (as in Example 2).

RELATED REFERENCES

1. Williams, B. A., *Surviving "Terminal" Cancer: Clinical Trials, Drug Cocktails, and Other Treatments Your Doctor Won't Tell You About.* 2002.
2. Williams, B. A., *Treatment Options for Glioblastoma and Other Gliomas.* 2013.
3. Botti, R. E., J. Triscari, H. Y. Pan, and J. Zayat, Concentrations of pravastain and lovastatin in cerebrospinal fluid in healthy subjects. *Clin Neuropharmacol,* 1991. 14(3): p. 256-261.
4. Soderberg-Naucler, C., A. Rahbar, and G. Stragliotto, Survival in patients with glioblastoma receiving valganciclovir. *New England Journal of Medicine,* 2013. 369 (10): p. 985-986.
5. Trouillas, P., J Honnorat, P. Bret, A. Jouvet, and J. P. Gerard, Redifferentiation therapy in brain tumors: long-lasting complete regression of glioblastomas and an anaplastic astrocytoma under long term 1-alpha-hydroxycholecalciferol. *J Neurooncol,* 2001. 51(1): p. 57-66.
6. Lissoni, P. and e. al, Increased survival time in brain glioblastomas by a radio-neuroendocrine strategy with radiotherapy plus melatonin compared to radiotherapy alone. *Oncology,* 1996. 53: p. 43-46.
7. Snipes, W, S. Person, A. Keith, and J. Cupp, Butylated hydroxytoluene inactivates lipid-containing viruses. *Science,* 1975. 188: p. 64-66.
8. Puri T., S. Goyal, P. K. Julka, O. Nair, D. N. Sharma, and G. K. Rath, Lycopene in treatment of high-grade gliomas: a pilot study. *Neurol India,* 2010. 58(1): p. 20-23.
9. Castino, R., A. Pucer, R. Veneroni, F. Morani, C. Peracchio, T. T. Lah, and C. Isidoro, Resveratrol reduces the invasive growth and promotes the acquisition of a long-lasting differentiated phenotype in human glioblastoma cells. *J Agricultural Food Chem,* 2011. 59: p. 4264-4272.
10. Juan, M E., M Maijo, and J. M. Planas, Quantification of trans-resveratrol and its metabolites in rat plasma and tissues by HPLC. *J Pharm Biomed Anal,* 2010. 51(2): p. 391-398.
11. Michelakis, E. D., G. Sutendra, P. Dromparis, L. Webster, A. Haromy, E. Niven, C. Maguire, T-L. Gammer, J. R. Mackey, D. Fulton, B. Abdulkarim, M. S. McMurtry, and K. C. Petrulc Metabolic modulation of glioblastoma with dichloroacetate. *Sci Transl Med.* 2(31): p. 1-8.
12. Sunayama, J, K-I. Matsuda, A. Sato, K Tachibana, K Suzuki, Y. Narita, S. Shibui, K Sakurada, T Kayama, A. Tomiyama, and C. Kitanaka, Crosstalk between the PI3K/mTOR and MEK/ERK pathway involved in the maintenance of self-renewal and tumorigenesis of glioblastoma stem-like cells. *Stem Cells,* 2010. 28: p. 1930-1939.
13. Larner, J., J. Jane, E. Lewis, R. Packer, C. Myers, and M. Shaffrey, A phase I-II trial of lovastatin for anaplastic astrocytomas and glioblastoma multiforme. *Am J Clin Oncol,* 1998. 21(6): p. 579-583.
14. Tabuzek, K, D. Suchy, B. Gabryel, A. Bielecka, S. Liber, and B. Okopien, Quantification of metformin by the HPLC method in brain regions, cerebrospinal fluid and plasma of rats treated with lipopolysaccharide. *Pharmacol Reports,* 2010. 62: p. 956-965.
15. Jiang, Z., X Zheng, R. A. Lytle, R. Higashikubo, and K. M. Rich, Lovastatin-induced up-regulation of the BH3-only protein, Bim, and cell death in glioblastoma cells. *J Neurochem,* 2004. 89: p. 168-178.

What is claimed is:

1. A method for the safe and effective treatment of inoperable malignant human gliomas, comprising administering a combination of an inhibitor of cytomegalovirus, alfacalcidol, and melatonin to human patients with at least one inoperable malignant glioma, such that reversal of the growth of said at least one inoperable malignant glioma occurs within two months after the onset of administration of the inhibitor of cytomegalovirus, alfacalcidol, and melatonin, wherein said malignant human gliomas are malignant astrocytomas.

2. The method of claim 1, further comprising administration of 100-2000 mg per day of butylated hydroxytoluene to said human glioma patients.

3. The treatment method of claim 1, further comprising administration of any or all of lycopene, curcumin, honokiol, and resveratrol to said human glioma patients.

4. The treatment method of claim 1, wherein the cytomegalovirus inhibitor is Valganciclovir.

5. The treatment method of claim 2, further comprising administration of any or all of lycopene, curcumin, honokiol, and resveratrol to said human glioma patients.

* * * * *